(12) United States Patent
Wu et al.

(10) Patent No.: US 7,365,127 B2
(45) Date of Patent: Apr. 29, 2008

(54) PROCESS FOR THE PREPARATION OF POLYMER CONJUGATES

(75) Inventors: Dechun Wu, Bridgewater, NJ (US); Hong Zhao, Edison, NJ (US); Richard B. Greenwald, deceased, late of Somerset, NJ (US); by Susan Adler, legal representative, Milwaukee, WI (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 362 days.

(21) Appl. No.: 11/051,009

(22) Filed: Feb. 4, 2005

(65) Prior Publication Data

US 2006/0178474 A1    Aug. 10, 2006

(51) Int. Cl.
*A61K 47/48* (2006.01)

(52) U.S. Cl. .............. 525/118; 525/54.1; 525/162; 424/178.1

(58) Field of Classification Search ........... 525/118, 525/162, 54.1; 424/178.1
See application file for complete search history.

(56) References Cited

U.S. PATENT DOCUMENTS

| | | | |
|---|---|---|---|
| 5,122,614 | A | 6/1992 | Zalipsky |
| 5,605,976 | A | 2/1997 | Matinez et al. |
| 5,643,575 | A | 7/1997 | Martinez et al. |
| 5,711,944 | A | 1/1998 | Gilbert et al. |
| 5,738,846 | A | 4/1998 | Greenwald et al. |
| 5,919,455 | A | 7/1999 | Greenwald et al. |
| 5,932,462 | A | 8/1999 | Harris et al. |
| 5,951,974 | A | 9/1999 | Gilbert et al. |
| 5,981,709 | A | 11/1999 | Greenwald et al. |
| 5,985,263 | A | 11/1999 | Lee et al. |
| 6,113,906 | A | 9/2000 | Greenwald et al. |
| 6,624,142 | B2 * | 9/2003 | Greenwald et al. ............ 514/2 |
| 6,774,180 | B2 | 8/2004 | Kozlowski et al. |

* cited by examiner

*Primary Examiner*—Randy Gulakowski
*Assistant Examiner*—Olga Asinovsky
(74) *Attorney, Agent, or Firm*—Lucas & Mercanti, LLP

(57) ABSTRACT

A process for efficiently preparing polymer conjugates such as branched PEG-polypeptide conjugates, in large scale without column chromatography clean up of the activated PEG linkers to remove impurities is disclosed.

30 Claims, 3 Drawing Sheets

PROCESS FOR THE PREPARATION OF POLYMER CONJUGATES

FIELD OF THE INVENTION

The present invention relates to an improved process for the preparation of polymer conjugates. In particular, the invention relates to an improved process for preparing and purifying polymer conjugates of biologically active moieties, such as proteins.

BACKGROUND

Conjugation of polymers to biologically active moieties such as proteins, polypeptides or small molecules has become increasingly popular over the years as a means of increasing the effectiveness while often decreasing one or more negative aspects of such moieties. In particular, polymer conjugation using a polyalkylene oxide (PAO) or more specifically, polyethylene glycol (PEG), has been widely accepted for designing effective derivatives of semi-toxic or immunogenic drugs for therapeutic use.

U.S. Pat. Nos. 5,643,575; 5,919,455; 5,605,976 to name a few, describe non-antigenic polymers, their preparation and methods of conjugating them with biologically active moieties. The contents of each of the foregoing are incorporated herein by reference. Although these patents provide valuable methods for improving the use of biologically active moieties such as enzymes, proteins and other peptides, and polypeptides, there still exists a need for improved methods of conjugation.

For example, the aforementioned '575 patent describes methods of making branched PEG derivatives and protein conjugates made therewith. One method described therein involves using an excess of a trifunctional molecule such as, lysine ethyl ester to conjugate with activated mPEG derivatives such as succinimidyl carbonate (SC)-mPEG. While this method provides the desired activated branched polymer and resulting conjugate, it has been found that there are certain circumstances under which it would be desirable to more economically provide the desired conjugates in levels of higher purity. In the past, some have suggested using column chromatography to remove any unreacted starting materials or by-products. See, for example, U.S. Pat. No. 5,932,462. Such techniques are costly, are inconvenient for large scale manufacturing and can result in a significant loss of yield. It would be highly desirable to eliminate or inactivate the remaining starting materials and by-products which can compete with the formation of the desired branched polymer-therapeutic conjugates before the final product is made. This in turn would reverse the loss of yield. Thus, alternatives have been sought, especially in cases of commercial production and where it is critical to minimize loss of the biologically active moiety.

The present invention provides a new and improved process for the preparation of activated PEG linkers and their subsequent conjugation to biologically active moieties. The present invention also serves an unmet need to provide an economically efficient conjugation process having improved purity and yield over the prior art.

SUMMARY OF THE INVENTION

In one embodiment of the invention there is provided a new process for preparing activated polymers and polymer conjugates made therewith. The first step in this aspect of the invention includes reacting an activatable polymer residue such as mPEG-OH with an activating agent capable of providing a leaving group on the activatable polymer residue and provide a first reaction mixture containing activated polymer residue, such as mPEG-succinimidyl carbonate (hereinafter SC-PEG) and a trace amount, preferably, of activatable polymer residue. Examples of activating agents as used herein include disuccinimidyl carbonate (DSC) or a combination of phosgene (or triphosgene) and N-hydroxysuccinimide (hereinafter NHS). Further activating agents/leaving groups are discussed below in the Detailed Description section.

The second step calls for reacting the first reaction mixture with a multi-functional linking moiety having at least one protecting group, i.e. a functional group being unreactive with the activated polymer residue, such as lysine ethyl ester. This second step is carried out under conditions wherein the activated polymer residue of the first reaction mixture is present in molar excess with respect to the active groups of the multi-functional linking moiety and thereby forms a second reaction mixture. This second reaction mixture contains the first reaction mixture and intermediate polymer, such as $(PEG)_2Lys$ ethyl ester, which results from reacting the activated polymer residue with the multi-functional linking moiety.

In the next step, the second reaction mixture is quenched with a first quenching reagent such as, phenethylamine or benzyl amine to the third reaction mixture to inactivate the activated polymer residue to form a third reaction mixture which contains inter alia the untermediate polymer conjugates. Then, a second quenching agent, such as, TBDMSiCl is added to the third reaction mixture to inactivate the activatable polymer residue therein and thus forms a fourth reaction mixture which contains inter alia the intermediate polymer conjugates. The first and second quenching agents can be added in any order so long as they are both not added at the same time. Preferably, however, the first quenching agent is added first and the second quenching agent is added thereafter.

The fourth reaction mixture is then treated with a deprotecting agent to remove the protecting group such as a strong base like LiOH to deprotect an ethyl ester or a strong acid such as TFA to deprotect a t-butyl ester. The intermediate polymer, i.e. a PEGylated multi-functional linking moiety, is then neutralized to form a fifth reaction mixture.

The fifth reaction mixture is then reacted with another activating agent or a compound capable of activating the intermediate polymer therein for linking to a biologically active moiety, such as NHS, to form a sixth reaction mixture. This sixth reaction mixture containing the activated polymer is then reacted with a biologically active moiety to form the desired polymer conjugate.

For purposes of the present invention, the process is described with regard to biologically active moieties. It will be understood however that this term also includes targeting and diagnostic agents. Unlike prior art processes, this sixth reaction mixture contains the desired activated polymer without competing intermediates for reacting with the biologically active moiety.

In another aspect of the invention, the desired polymer conjugates are isolated from the final reaction mixture such as via diafiltration, size exclusion, ion exchange column, affinity column or other techniques well-known to those of ordinary skill. It will be understood that the choice of isolation technique depends on the individual final conjugate formed, such choice can be made without undue experimentation.

As a result of the invention, the artisan is provided with a process which provides a desired polymer conjugate efficiently and in high yield. It is easily adaptable to large batch or commercial scale-up, with the costly and time consuming step of column chromatography to isolate the desired activated PEG linker being avoided. In one particularly preferred embodiment in which (PEG)$_2$ Lys-polypeptide conjugates are made, the preferred quenching agents form mPEG amine carbamate and silyl-blocked mPEG, both of which are inert toward the polypeptide conjugation and easily separable from the final PEG-polypeptide conjugates during purification.

Other and further advantages will be apparent to those of ordinary skill without undue experimentation from the description provided herein.

DETAILED DESCRIPTION

A. Overview

Figure 1:
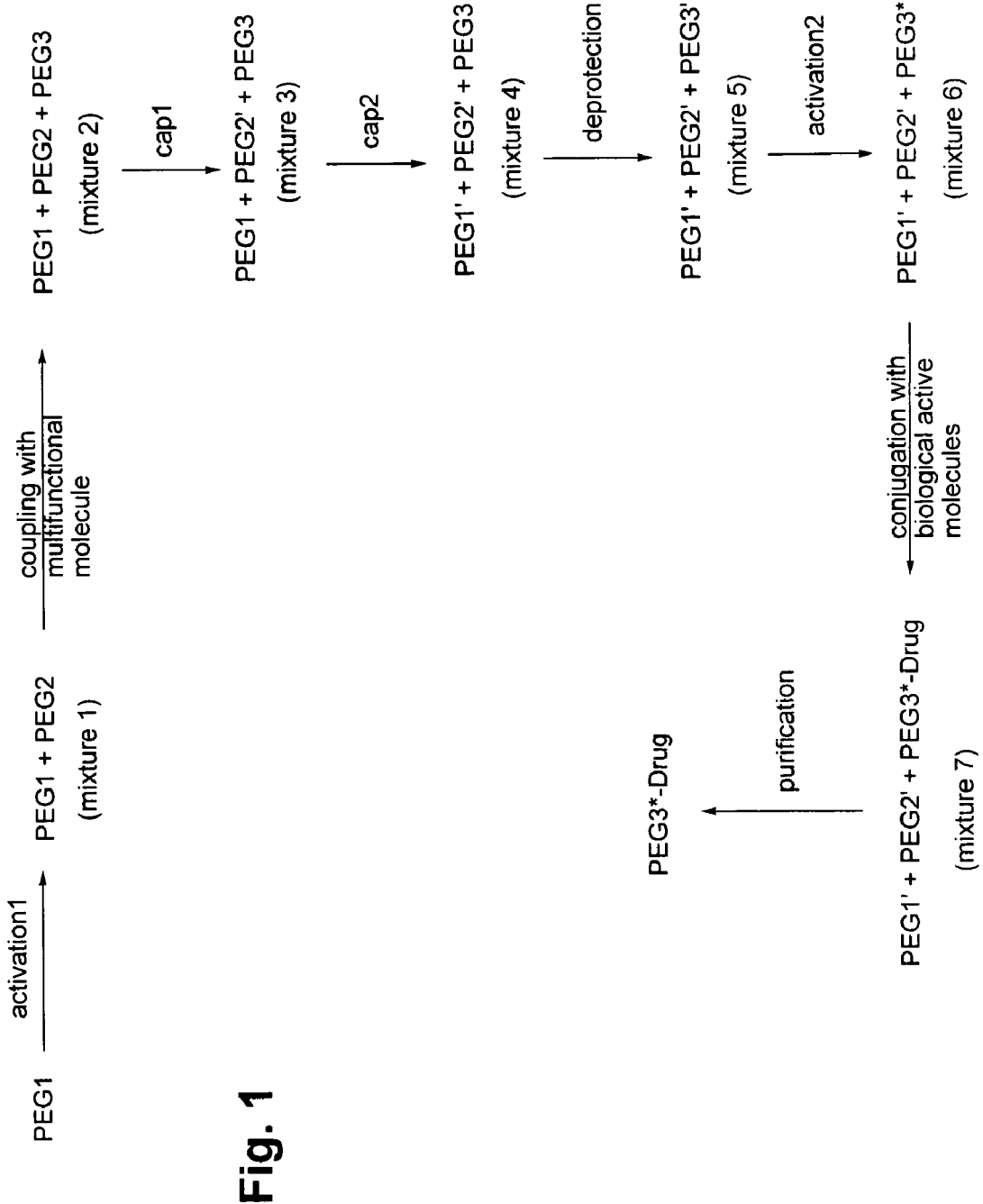
FIG. 1 schematically illustrates reactive steps described in the specification.

The processes of the present invention are useful for preparing a wide variety of polymer (PEG) conjugates. Although there is considerable latitude in the selection of the various components of the reaction mixtures made in the course of the present invention, the characteristics of the components at each stage are similar enough so that a general description of the process is possible. Reference is now made to FIG. 1 where a schematic representation of the reactions described hereinbelow is provided.

B. First Reaction Mixture

The first reaction mixture is formed using well-known polymer or PEG activation techniques. This results in a solution containing, i.e. an activatable polymer residue, such as PEG-OH, and an activated polymer residue, such as SC-PEG. Excess small molecule reagents can be easily removed using known techniques such as recrystallization.

For purposes of the present invention, activatable polymer residues can include any such known compounds but in preferred aspects of the invention, polyalkylene oxide (POA) or polyethylene glycol (PEG) based compounds are used. A non-limiting list of such compounds include mPEG-OH, mPEG-NH$_2$, mPEG-CO$_2$H, mPEG-SH, and mPEG-halogen, e.g. Cl. In more preferred embodiments, the activatable polymer residue is mPEG-OH.

Where mentioned with regard to the synthesis of the polymer conjugates described herein, suitable leaving groups include, without limitation, moieties such as N-hydroxybenzotriazolyl, halogen, N-hydroxyphthalimidyl, p-nitrophenoxy, imidazolyl, N-hydroxysuccinimidyl, thiazolidinyl thione, or other good leaving groups as will be apparent to those of ordinary skill. For purposes of the present invention, leaving groups are to be understood as those groups which are capable of being replaced by a nucleophilic group such as an NH$_2$, OH, SH or other reactive amino group (nucleophile) found on a multifunctional molecule.

Examples of preferred activating agents capable of providing a leaving group on the polymer residue include without limitation DSC/Pyridine or NHS/triphosgene to make SC-PEG, 2-mercaptothiozolidine/EDC/DMAP to make T-PEG, (i.e. PEG-2-mercaptothiozolidinyl carbamate), N-hydroxyphthalamidyl/DMAP to make BSC-PEG (i.e. PEG-N-hydroxyphthalamidyl carbonate, etc.)

Examples of some preferred activated polymer residues useful in the process of the invention include those well known to those of ordinary skill in the PEGylation art. Many are commercially available for example from Nektar of Huntsville, Ala. A non-limiting list of suitable activated polymer residues include

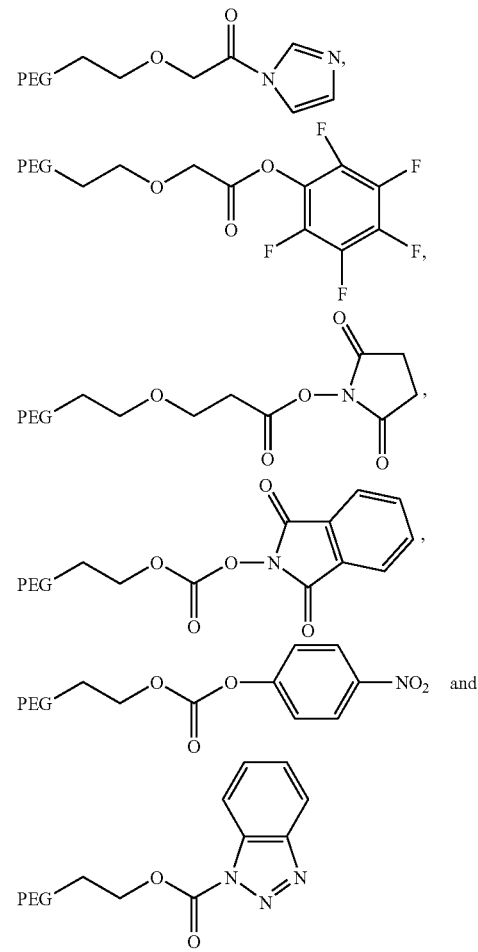

while others will be apparent to those of ordinary skill. In more preferred aspects, the activated polymer residue is SC-mPEG. Even if the activated polymer residues are purchased from a vendor, it is likely that there will be either some trace amounts of impurities, i.e. mPEG-OH or some of the PEG-OH generated during the course of the reaction. Thus, the quenching of the PEG-OH or other starting material should be employed in reaction mixtures made with such compounds.

In general, the reaction takes place at about room temperature, in an inert solvent such as tetrahydrofuran (THF), toluene (TOL), methylene chloride (DCM), chloroform (CHCl$_3$), dimethyl formamide (DMF) or mixtures thereof.

C. Second Reaction Mixture

After the first reaction mixture is formed, it is reacted with a multi-functional linking moiety having at least one functional group being un-reactive with the activated polymer residue. The reaction is carried out under conditions in which the activated polymer residue found in the first reaction mixture is present in preferably a molar excess with respect to the multi-functional linking moiety.

Generally, the reaction is carried out at about room temperature. When the preferred SC-PEG is used, however formation of the second reaction mixture is preferably carried out at temperatures of from about 20 to about 50° C. and more preferably from about 25 to about 35° C.

While lysine and lysine esters such as lysine ethyl ester are two of the more well known and preferred multi-functional linking moieties having at least one protecting group, i.e. a functional group being un-reactive with the activated polymer residue, those of ordinary skill will of course realize that other compounds are also useful. For example, 1,3-diamino-2-propanol, diethylenetriamine, malonyl chloride and others can be used. A non-limiting list of such alternatives generally include substituted alkyl diamines, triamines, natural and unnatural amino acid derivatives such as malonic ester derivatives and dihydroxy-alkyls or dithioaklyls.

The resultant reaction results in the formation of the second reaction mixture which contains the first reaction mixture and newly created intermediate polymer conjugates which result from the reacting of the activated polymer residue with the multi-functional linking moiety.

D. Third and Fourth Reaction Mixtures

After the intermediate polymer conjugate has been formed, a first and a second quenching agent are separately added to the second reaction mixture to form the third and fourth reaction mixtures, respectively.

Specifically, the third reaction mixture can be formed by reacting the second reaction mixture with a first quenching agent to inactivate the activated polymer residue therein. Thereafter, a second quenching agent is added to the third reaction mixture to inactivate the activatable polymer residue therein and form a fourth reaction mixture. The fourth reaction mixture thus includes 1) an intermediate polymer which will be activated for linking to targets of interest (in subsequent steps), 2) inactivated starting materials and 3) byproducts which would otherwise be competing with the desired activated polymer linker when the biologically active protein, polypeptide, etc. is reacted therewith.

In an alternative embodiment of the invention, the third reaction mixture is made by reacting the second reaction mixture with the second quenching agent so that the activatable polymer residue therein is inactivated first. This alternative third reaction mixture is then reacted with the first quenching agent to inactivate the activated polymer residue therein and form an alternative fourth reaction mixture.

The amount of quenching agents used is referred to as a sufficient amount. For purposes of the present invention, a "sufficient" amount of the agents is an amount which inactivates the activated polymer residue therein, for the first quenching agent and, for the second quenching agent, an amount which is sufficient to inactivate the activatable polymer residue therein.

Suitable first quenching agents are those compounds containing a free amine, free thiol or free hydroxyl group such as cysteine, benzyl amine, n-butyl amine, phenylethylamine, C-terminal blocked amino acids such as, blocked glycine or blocked alanine and mixtures thereof.

The selection of the first quenching agent will, of course, depend upon the nature of the activated polymer residue (i.e. mPEG-SC, etc.) employed in the process. Suitable second quenching agents include those compounds containing a silyl group or an acid chloride and capable of reacting with the activatable polymer residue found therein.

The selection of second quenching agent again depends upon the nature of the activatable polymer residue (i.e. mPEG-OH, mPEG-NH$_2$, etc.) employed in the process. A non-limiting list of suitable agents include tetra-butyl dimethyl silylchloride (TBDMSiCl), tri-methyl silylchloride (TMSiCl) MeI, MeSO$_4$, CF$_3$SO$_3$Me, Me$_3$OBF$_4$. For example, when mPEG-OH is used, the preferred second quenching agent is TBDMSiCl.

F. Fifth Reaction Mixture

The protecting group on the intermediate polymer in the forth reaction mixture is deprotected using an effective amount of a deprotecting agent, i.e. a strong acid or a strong base. Suitable bases include but are not limited to, lithium hydroxide, potassium hydroxide, potassium t-butoxide, butyl lithium, and sodium amide. Suitable acids can be selected from trifluoroacetic acid (TFA), sulfuric, phosphoric and hydrochloric acids, and the like. Preferably, lithium hydroxide is added to deprotect, followed by neutralization with hydrochloric acid. Thereafter, the forth mixture is neutralized to form the fifth reaction mixture.

The fifth reaction mixture is then activated by reacting with an appropriate activating agent, that is, it is reacted with a compound capable of activating the intermediate polymer conjugates therein for linking to a biologically active moiety. This step causes the sixth reaction mixture containing an activated polymer therein to be formed. Examples of suitable compounds capable of activating the intermediate include those "activating agents" mentioned above in the formation of the first reaction mixture. When it is desirable to allow the activated polymer to attach to amino groups of a target, the preferred leaving group is NHS.

G. Polymer Conjugates

The sixth reaction mixture contains the two inactivated polymer residues and one activated branched polymer linker which is now suitable for reacting with the target biologically active agent without further purification, and form the polymer conjugates. These activated branched polymers can be those described in the previously mentioned, commonly assigned U.S. Pat. Nos. 5,643,575, 5,919,455 and 6,113,906. One particularly preferred activated branched polymer is:

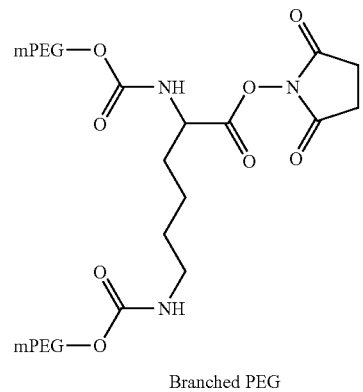

Branched PEG

The polymer conjugates containing leaving groups, biologically active compounds, targeting moieties, or diagnostic agents which result from the process of the invention are generally of the formula:

(R)$_n$-L-D wherein:

R is a polymer residue;

L is a multi-functional linking moiety such as lysine, diaminopropanol, suitable amino acids, with or without aromatic groups included;

D is a member of the group consisting of leaving groups, biologically active moieties, targeting moieties and diagnostic agents; and n is a positive integer, preferably 2.

More preferably, the conjugates correspond to one of the following formulae:

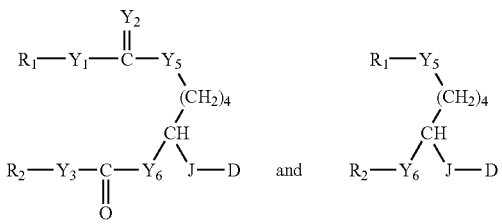

wherein $R_{1-2}$ are the same or different polymeric residues;

$Y_{1-6}$ are independently O, S, or $NR_3$, wherein $R_3$ is selected from among H (preferred), $C_{1-6}$ alkyls and substituted alkyls, $C_{3-6}$ branched alkyls and substituted branched alkyls and $C_{4-8}$ cycloalkyls;

J is a bifunctional linking moiety; and

D is a leaving group, biologically active compound, targeting moiety or diagnostic agent. Within this aspect, $Y_2$ and $Y_4$ are preferably O, while $Y_1$, $Y_3$, $Y_5$ and $Y_6$ are either O, S or NH.

Still further polymer conjugates of the invention include:

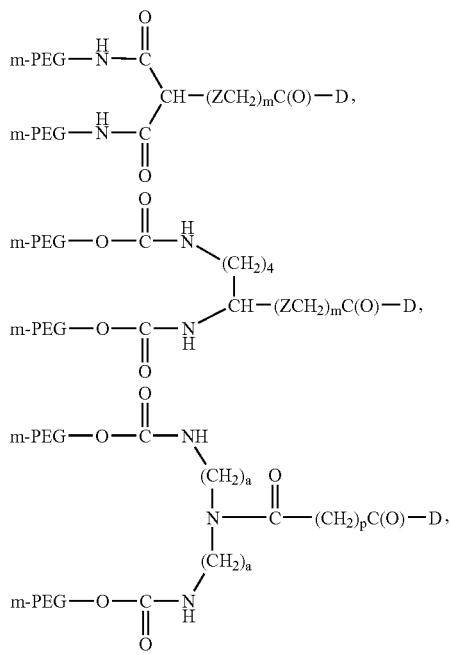

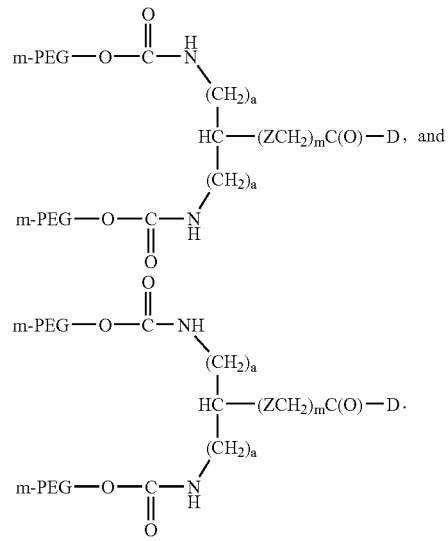

wherein:

(a) is an integer of from about 1 to about 5;

Z is O, $NR_4$, S, SO or $SO_2$; where $R_4$ is H, $C_{1-8}$ alkyl, $C_{1-8}$ branched alkyl, $C_{1-8}$ substituted alkyl, aryl or aralkyl;

(m) is 0 or 1;

(p) is a positive integer, preferably from about 1 to about 6, and

D is a leaving group, biologically active compound, a targeting moiety or a diagnostic agent.

Polymer Residues

As stated above, R, $R_1$ and $R_2$ are polymer residues. Preferably, each is a water soluble polymer residue which is preferably substantially non-antigenic such as polyalkylene oxide (PAO's) and more preferably polyethylene glycol. For purposes of illustration and not limitation, the polyethylene glycol (PEG) residue portion can be selected from among:

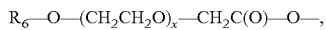

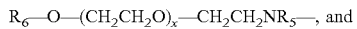

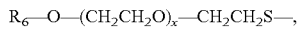

wherein:

x is the degree of polymerization i.e. from about 10 to about 2,300;

$R_5$ is selected from among hydrogen, $C_{1-6}$ alkyls, $C_{2-6}$ alkenyls, $C_{2-6}$ alkynyls, $C_{3-12}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxy, and $R_6$ is a capping group, i.e. methyl, ethyl, benzyl, etc.

In one particularly preferred embodiment, R is selected from among

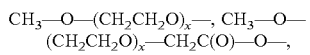

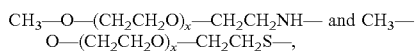

where x is a positive integer, selected so that the total weight average molecular weight is from about 200 to about 120, 000 Da (dalton). Preferably, the total weight average molecular weight is from about 2,000 to about 80,000 Da, with from about 10,000 to about 40,000 Da being more preferred. In many aspects the most preferable total molecular weight of the polymer portion of the conjugate is from about 5,000 to about 40,000 Da, depending upon the needs of the artisan.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

Bifunctional Linking Moieties "J"

J can be any linking group in which facilities attachment of the biolically active moiety to the aliphatic linking group. A non-limiting list includes:

—NHC(O)CH$_2$OCH$_2$C(O)—;

—NHC(O)CH$_2$NHCH$_2$CH(O)—;

—NHC(O)CH$_2$SCH$_2$C(O)—;

—NHC(O)CH$_2$CH$_2$CH$_2$C(O)—; or

—NHC(O)CH$_2$CH$_2$C(O)—;

wherein $R_7$, $R_8$ and $R_9$ and selected from the same group which defines $R_6$; and t is a positive integer, preferably from about 1 to about 12.

H. Separation of the Polymer Conjugates

In another aspect, the process above further comprises a step of separating or isolating the polymer conjugate from the by-products in mixture 7. This can be done using any art accepted process which is suitable for accomplishing the result. Preferably, the process employed is one which can be used in commercial settings with efficiency. It is contemplated that diafiltration or size exclusion chromatography will be most often used to achieve the desired result. However, ion exchange, affinity, and hydrophobic column chromatography can also be used depending on the individual needs of the artisan. For example, the reaction mixture can be diluted with water and loaded onto a column packed with SP Sepharose FF resin. The column is then washed with a suitable buffer such as a PBS (phophate) buffer to remove all inert PEG's plus the PEGhydrolyzed during the reaction. Next, the polymer conjugates with two or more sites attached are washed out with a different gradient of the buffer before the desired polymer conjugates are eluted with high, eg. >90-95% purity.

Biologically Active Moieties

In those aspects of formula (I) where D is a biologically active compound, a non-limiting list of such suitable compounds include residues of organic compounds, enzymes, proteins, polypeptides, etc. In addition to the foregoing, the biologically active compound can also be a residue of an enzyme, protein, polypeptide, monoclonal antibodies, oligonucleotides, immunoconjugates, such as, SS1P, single chain antigen binding proteins (SCA's), such as, CC49, and fragments thereof are also contemplated. Suitable proteins include but are not limited to, polypeptides, enzymes, peptides and the like having at least one available group for polymer attachment, e.g. an ε-amino, cystinylthio, N-terminal amino, including materials which have physiological or pharmacological activities as well as those which are able to catalyze reactions in organic solvents.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, etc., α, β and γ interferons, colony stimulating factors including granulocyte colony stimulating factors, platelet derived growth factors and phospholipase-activating protein (PLAP) as well as Thymosin alpha 1 and Secretin. Other proteins of general biological or therapeutic interest include insulin, plant proteins such as lectins and ricins, tumor necrosis factors and related proteins, growth factors such as transforming growth factors, such as TGFα or TGFβ, VEGF, TNFα, viral protein chemokines, and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a biological polymer demonstrating in vivo bioactivity. This includes amino acid sequences, nucleic acids (DNA, RNA), peptide nucleic acids (PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino- or hydroxyl-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds/compositions can be similarly modified without undue experimentation. It is to be understood that those biologically active materials not specifically mentioned but having suitable attachment groups are also intended and are within the scope of the present invention.

Diagnostic Agents

In those aspects of formula (I) where D is a diagnostic agent, a non-limiting list of suitable agents includes dyes, chelating agents, and isotope labeled compounds and other labeling compounds such as Green Fluorescent Protein (GFP).

Targeting Moieties

In those aspects of formula (I) where D is a targeting moieties, a non-limiting list of suitable agents includes, peptides such as, TAT peptide and U-7 peptide, single chain antibodies such as, CC49, and small molecules, such as, for example, taurine and biotin.

In a preferred aspect of the invention, the biologically active compound is a compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds/compositions can be similarly modified without undue experimentation. It is to be understood that those biologically active materials not specifically mentioned but having suitable attachment groups are also intended and are within the scope of the present invention.

H. In Vivo Diagnostics

In another aspect of the invention the diagnostic agent is a tag selected for diagnostic or imaging purposes. Thus, a suitable tag is prepared by linking any suitable moiety, eg., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In a still further aspect of the invention, the inventive tagged conjugates are readily prepared, by art-known methods, with any suitable label, including, e.g., radioisotope labels. Simply by way of example, these include $^{131}$Iodine, $^{125}$Iodine, $^{99m}$Technetium and/or $^{111}$Indium to produce radioimmunoscintigraphic agents for selective uptake into tumor cells, in vivo. For instance, there are a number of art-known methods of linking peptide to Tc-99 m, including, simply by way of example, those shown by U.S. Pat. Nos. 5,328,679; 5,888,474; 5,997,844; and 5,997,845, incorporated by reference herein. Other radioisotopes such as $^{14}$C, $^{15}$N, etc. can also be used.

Broadly, for anatomical localization of tumor tissue in a patient, the conjugate tag is administered to a patient or animal suspected of having a tumor. After sufficient time to allow the labeled immunoglobulin to localize at the tumor site(s), the signal generated by the label is detected, for instance, visually, by X-ray radiography, computerized transaxial tomography, MRI, by instrumental detection of a luminescent tag, by a photo scanning device such as a gamma camera, or any other method or instrument appropriate for the nature of the selected tag.

The detected signal is then converted to an image or anatomical and/or physiological determination of the tumor site. The image makes it possible to locate the tumor in vivo and to devise an appropriate therapeutic strategy. In those embodiments where the tagged moiety is itself a therapeutic agents, the detected signal provides evidence of anatomical localization during treatment, providing a baseline for follow-up diagnostic and therapeutic interventions.

EXAMPLES

Figure 2:
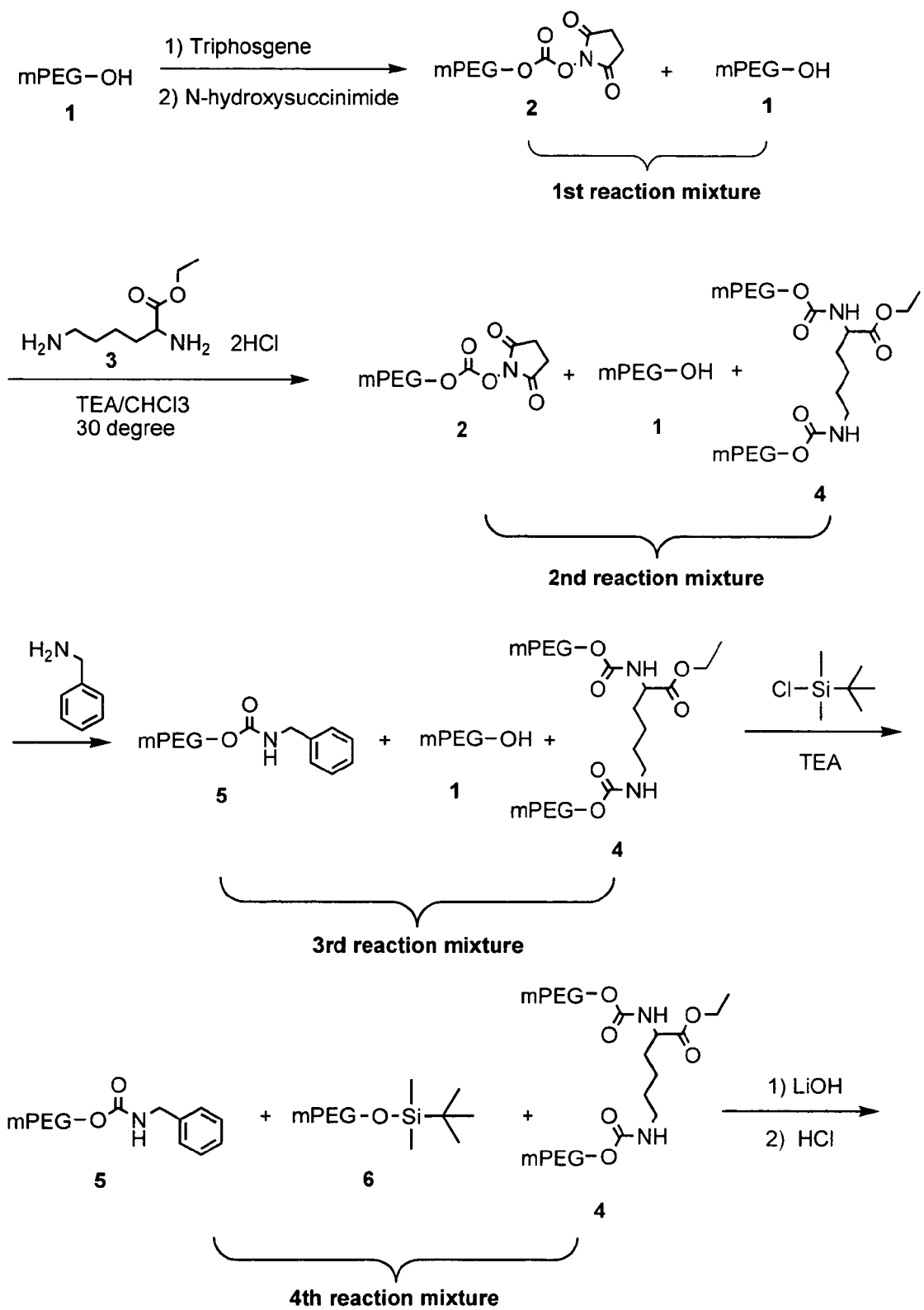
FIGS. 2-3 schematically illustrate reaction schemes described in the Examples.
Figure 3:
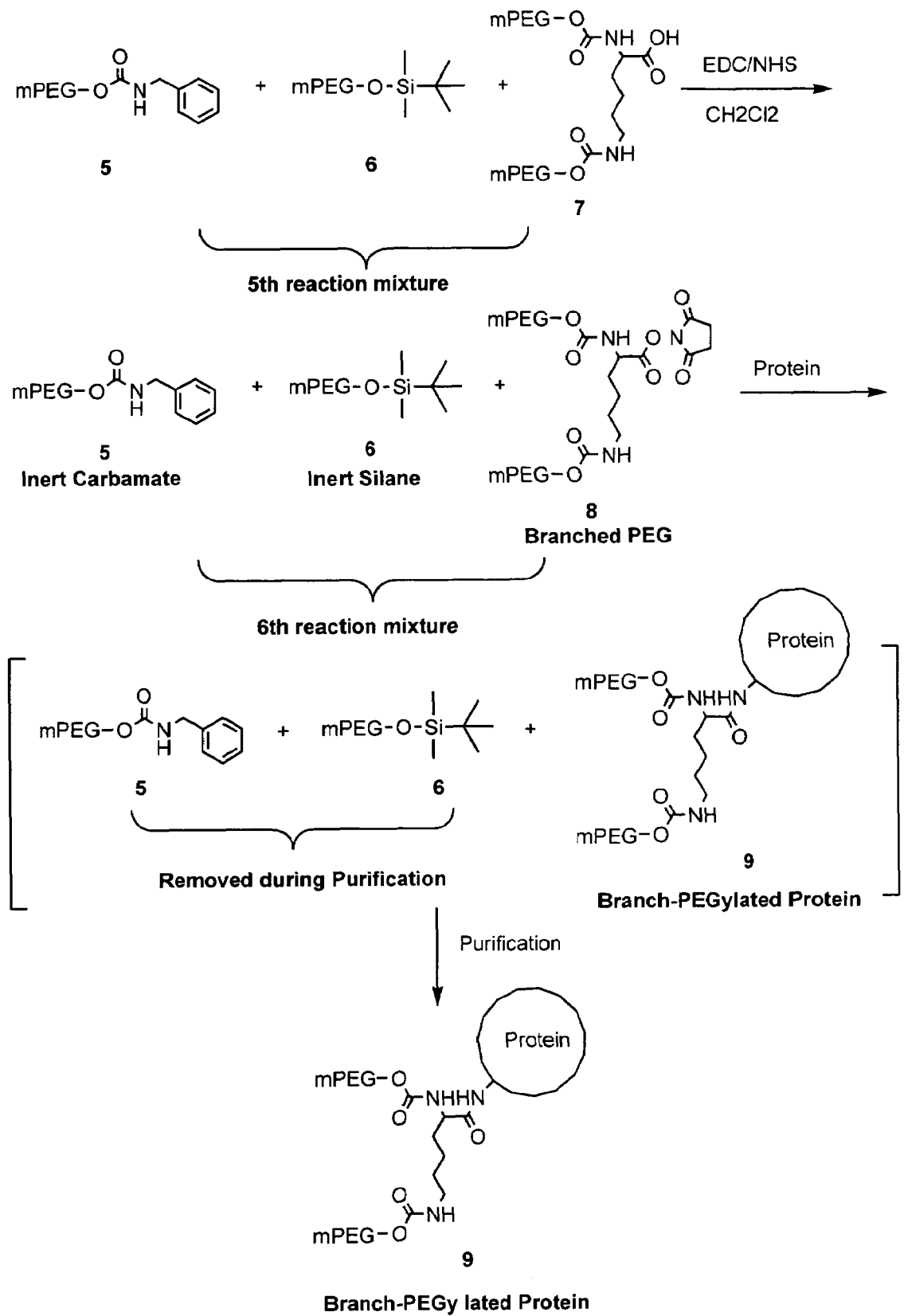

The following examples serve to provide further appreciation of the invention but are not meant in any way to restrict the effective scope of the invention. The reference numerals provided in bold correspond to the compounds shown in FIGS. 2-3.

PEG2 Synthesis

Example 1

First Reaction Mixture:

Compound 1 20 k mPEG-OH (125 g, 6.24 mmol) was azeotroped with toluene (1.88 l) under nitrogen for two hours to remove 375 ml of solvent. The solution was cooled to 50° C. Triphosgene (1.24 g, 4.18 mmol) and pyridine (0.99 g, 12.47 mmol) were added and reaction solution was stirred at 50° C. for three hours. N-hydroxysuccinimide (1.79 g, 15.59 mmol) and pyridine (1.23 g, 15.59 mmol) were then added. The reaction solution was stirred at 50° C. over twenty hours followed by filtration to remove pyridine salt. The toluene solvent was completely removed under vacuum at 40° C. The residue was dissolved in dry dichloromethane (400 ml). Ethyl ether (2.50 l) was added slowly to the solution to precipitate the product. This crude product was redissolved in acetonitrile (875 ml) followed by slow addition of isopropyl alcohol (3.75 l) to precipitate white solids. The solids were filtered and washed with isopropyl alcohol and ether. The isolated solids were dried at 40° C. under vacuum to give the first reaction mixture which contained compounds 1 and 2 (112 g, 5.55 mmol, 89%). $^{13}$C NMR (75.5 MHz, CDCl$_3$) δ 25.0, 58.6, 67.9-71.4 (PEG), 151, 168.1.

Example 2

Second and Third Reaction Mixtures:

The first reaction mixture of compound 1 and 2 (5.0 g, 0.25 mmol) was dissolved in anhydrous chloroform (50 ml) under nitrogen. l-lysine ethyl ester dihydrochloride (26 mg, 0.10 mmol) and triethylamine (42 mg, 0.41 mmol) were added. The reaction solution was heated to 30° C. and stirred at 30° C. for twenty hours to give the second reaction mixture containing compounds 1, 2 and 4. This second reaction mixture was cooled to room temperature followed by the addition of benzylamine (53.2 mg, 0.50 mmol) to quench excess activated PEG of the first reaction mixture. This reaction solution was stirred at room temperature for twenty hours. Solvent was removed at 30° C. under vacuum. The residue was dissolved in dry dichloromethane (15 ml). Ethyl ether (100 ml) was added slowly to the solution to precipitate the product. This crude product was redissolved in acetonitrile (10 ml) followed by slow addition of isopropyl alcohol (150 ml) to precipitate white solids. The solids were filtered and washed with isopropyl alcohol and ether. The isolated solids were dried at 40° C. under vacuum to give the third reaction mixture of compound 1, 4 and 5 (4.5 g, 90 % by weight). $^{13}$C NMR (75.5 MHz, CDCl$_3$) δ 13.84, 21.91, 29.06, 31.70, 40.06, 44.38 (benzyl amine), 53.27, 58.55, 60.85, 63.26, 63.71, 68.97-71.41 (PEG), 126.88-127.95 (benzyl amine), 155.32, 155.88, 171.60.

Example 3

Fourth Reaction Mixture:

The third reaction mixture containing compounds 1, 4 and 5 (4.23 g) was dissolved in anhydrous dichloromethane (40 ml) followed by the addition of tert-butyl-dimethylsilyl chloride (8 mg, 0.05 mmol) and triethylamine (26 mg, 0.26 mmol). The reaction solution was stirred at room temperature under nitrogen for twenty hours. Solvent was removed under vacuum. The residue was dissolved in dry dichloromethane (15 ml). Ethyl ether (100 ml) was added slowly to the solution to precipitate the product. This crude product was redissolved in acetonitrile (10 ml) followed by slow addition of isopropyl alcohol (125 ml) to precipitate white solids. The solids were filtered and washed with isopropyl alcohol and ether. The isolated solids were dried at 40° C. under vacuum to give fourth reaction mixture of compound 4, 5 and 6 (3.8 g, 93% by weight). $^{13}$C NMR (75.5 MHz, CDCl$_3$) δ13.79, 21.85, 28.98, 31.59, 39.99, 44.38 (benzyl amine), 53.20, 58.49, 60.76, 63.20, 63.64, 68.91-71.37 (PEG), 126.84-127.89 (benzyl amine), 155.29, 155.84, 171.54.

Example 4

Fifth Reaction Mixture:

The fourth reaction mixture of compounds 4, 5 and 6 (3.46 g) was dissolved in water (20 ml) completely. Lithium hydroxide monohydrate (5.4 mg, 0.13 mmol) was added and reaction solution was stirred at room temperature for twenty hours. The pH of the solution was adjusted to 2 to 2.5 followed by the extraction with dichloromethane (100 ml) twice. The combined organic layer was dried with magnesium sulfate. Solvent was removed under vacuum. The residue was dissolved in dry dichloromethane (15 ml). Ethyl ether (100 ml) was added slowly to the solution to precipitate the product. The solids were filtered and washed with ether. The isolated solids were dried at 40° C. under vacuum to give the fifth reaction mixture containing compounds 5, 6 and 7 (3.0 g, 87% by weight). $^{13}$C NMR (75.5 MHz, CDCl3) δ 21.8, 28.98, 31.62, 40.06, 44.50 (benzyl amine), 52.88, 58.55, 63.23, 63.63, 65.29-72.27 (PEG), 126.87-127.95 (benzyl amine), 155.29, 155.84, 172.40.

Example 5

Sixth Reaction Mixture:

The fifth reaction mixture containing compounds 5, 6 and 7 (2.22 g), N-hydroxysuccinimide (38 mg, 0.33 mmol) and N,N-diisopropylethylamine (85 mg, 0.66 mmol) were dissolved in a mixture solvent of anhydrous dichloromethane and N,N-dimethyl-formamide under nitrogen. The solution was cooled to 0° C. with ice bath and 1-[3-(dimethylamine) propyl]-3-ethylcarbodiimide hydrochloride was added. The reaction solution was stirred overnight from 0° C. to room temperature. Solvent was removed under vacuum. The residue was dissolved in dry dichloromethane (7 ml). Ethyl ether (50 ml) was added slowly to the solution to precipitate the product. This crude product was redissolved in acetonitrile (4.5 ml) followed by slow addition of isopropyl alcohol (70 ml) to precipitate white solids. The solids were filtered and washed with isopropyl alcohol and ether. The isolated solids were dried at 40° C. under vacuum to give the sixth reaction mixture containing compounds 5, 6 and 8 (2.07 g, 93% by weight). $^{13}$C NMR (75.5 MHz, CDCl3) δ 21.46, 25.17, 28.80, 31.38, 39.74, 44.44 (benzyl amine), 51.72, 58.55, 63.34, 64.03, 69.12-71.41 (PEG), 126.93-127.95 (benzyl amine), 155.07, 155.97, 167.51, 168.19.

Example 6

PEG$_2$-IFN β-1b (Mono PEGylated PEG$_2$ Interferon β-1b)

Pegylated IFN β-1b (Mono PEGylated PEG$_2$ Interferon β-1b) was synthesized by the reaction of pure IFN β-1b (5 ml of 0.45 mg/ml) in 50 mM sodium phosphate, 50 mM sodium chloride, 0.05% Zwittergent 3-14, pH=7.9 with the sixth reaction mixture containing compound 5, 6 and 8 (38 mg). Reaction mixture was stirred for 1.5 hours at 25° C. The PEGylation reaction was quenched by adding glycine (9.5 μl of 1 M glycine solution) and then lowering the pH to 6.5 with 2N acetic acid. The mono-PEGylated conjugate compound 9 (branched-PEGylated protein) was obtained with yield of 39% according to RP-HPLC (see Table 1.). There is no straight chain PEGylated (½ PEG) IFN β-1b. The following procedure was used to isolate pure mono PEGylated IFN β-1b compound 9.

The quenched reaction mixture was diluted with water to adjust the conductivity to ~5 ms and then loaded onto a column packed with SP Sepharose FF resin, previously equilibrated with 20 mM sodium phosphate, pH 6.5, at flow rate of 5 ml/min. Column was washed with the equilibration buffer to remove all the inert PEGs from sixth reaction mixture plus the PEG hydrolyzed during the reaction. The PEG$_2$-IFN β-1b oligomers (HiPEG) were washed out with 75 mM sodium chloride in equilibration buffer for 10 column volumes. The desired mono PEGylated PEG$_2$-IFN β-1b compound 9 was then eluted with 225 mM sodium chloride in the equilibration buffer for 10 column volumes. The final isolated yield was about 30%, based on IFN-β.

TABLE 1

RP-HPLC Analysis after PEGylation

| | Area of Peak | | | | Yield (%) | | | |
|---|---|---|---|---|---|---|---|---|
| | Native | Mono-PEG | Hi-PEG | ½ PEG | Mono-PEG | Hi-PEG | Native | ½ PEG |
| PEG-IFN-β-1b Reaction Mix | 4537.52 | 3035.75 | 275.297 | 0 | 39 | 4 | 58 | 0 |

Note:
MonoPEG = Mono PEGylated PEG$_2$-IFN β-1b;
HiPEG = Di/Tri PEGylated PEG$_2$-IFN β-1b;
Native = IFN β-1b;
½ PEG = Straight chain PEG-IFN β-1b.

Example 7

A comparative PEGylated IFN β-1b was prepared using PEG$_2$-NHS of the same molecular weight from Nektar in place of the branched activated PEG 8 and sixth reaction mixture used in Example 6, with the same conjugation conditions. This comparative PEG$_2$-NHS was purified using column chromatography prior to reacting with the interferon. RP-HPLC analysis was again conducted after PEGylation. The results are shown below in Table 2.

TABLE 2

| | RP-HPLC Analysis after PEGylation | | | | | | | |
|---|---|---|---|---|---|---|---|---|
| | Area of Peak | | | | Yield (%) | | | |
| | Native | Mono-PEG | Hi-PEG | ½ PEG | Mono-PEG | Hi-PEG | Native | ½ PEG |
| PEG-IFN-β-1b Prior art | 4772.82 | 4884.72 | 792.17 | 0 | 47 | 8 | 46 | 0 |

The results above demonstrate that the process of the present invention provides favorable results when compared to prior art processes without the added costs required column purification of the PEG$_2$-NHS prior to reaction with the interferon. The Hi-PEG (multi-PEG) portion obtained as a result of the inventive process was significantly less than that found with the commercially available PEG$_2$-NHS. The percent yield for the Hi-PEG was reduced by about half as a result of the novel process.

We claim:

1. A process for preparing an activated polymer having a multifunctional linking moiety thereon, comprising:
   a) reacting an activatable polymer residue with an activating agent capable of providing a leaving group thereon to provide a first reaction mixture containing an activated polymer residue and said activatable polymer residue;
   b) reacting said first reaction mixture with a multi-functional linking moiety having a protecting group thereon which is unreactive with said activated polymer residue under conditions wherein said activated polymer residue of the first reaction mixture is present in excess with respect to said multi-functional linking moiety to form a second reaction mixture containing said first reaction mixture and an intermediate polymer containing the protecting group resulting from said reacting of said activated polymer residue with said multi-functional linking moiety;
   c) quenching said second reaction mixture with a sufficient amount of a first quenching agent to inactivate the activated polymer residue therein forming a third reaction mixture containing said intermediate polymer;
   d) adding a sufficient amount of a second quenching agent to said third reaction mixture to inactivate the activatable polymer residue therein and form a fourth reaction mixture containing said intermediate polymer;
   e) removing the protecting group from the intermediate polymer and neutralizing said fourth reaction mixture to form a fifth reaction mixture containing a deprotected intermediate polymer; and
   f) reacting said fifth reaction mixture with a compound capable of activating the deprotected intermediate polymer therein for linking to a biologically active moiety and form a sixth reaction mixture containing an activated polymer having a multifunctional linking moiety thereon.

2. The process of claim 1, further comprising reacting said sixth reaction mixture with a biologically active compound, targeting moiety or diagnostic agent to form polymer conjugates.

3. The process of claim 2, further comprising isolating polymer conjugates.

4. The process of claim 3, wherein said isolating is carried out by diafiltration or size exclusion chromatography.

5. The process of claim 2, wherein the polymer conjugates are of the formula:

(R)$_n$-L-D wherein:
   R is a polymer residue;
   L is a multi-functional aliphatic linking moiety;
   D is a member of the group consisting of biologically active moieties, targeting moieties and diagnostic agents; and
   n is a positive integer.

6. The process of claim 5, wherein R is a polyalkylene oxide.

7. The process of claim 6, wherein said polyalkylene oxide is polyethylene glycol.

8. The process of claim 7, wherein said polyethylene glycol has a weight average molecular weight of from about 200 to about 120,000 daltons.

9. The process of claim 8, wherein said polyethylene glycol has a weight average molecular weight of from about 2,000 to about 80,000 daltons.

10. The process of claim 9, wherein said polyethylene glycol has a weight average molecular weight of from about 10,000 to about 40,000 daltons.

11. The process of claim 1, wherein said activatable polymer residue is selected from the group consisting of mPEG-OH, mPEG-NH$_2$, mPEG-CO$_2$H, mPEG-SO$_2$, and mPEG-halogen.

12. The process of claim 11, wherein said activatable polymer residue is mPEG-OH.

13. The process of claim 1, wherein said activated polymer residue is selected from the group consisting of

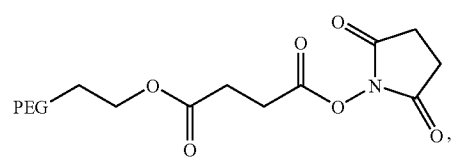

-continued

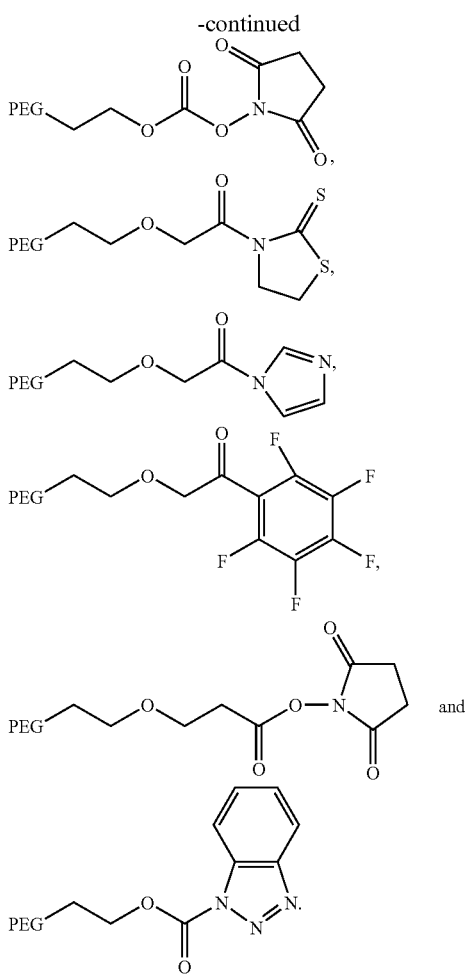

14. The process of claim 13, wherein the activated polymer residue is SC-PEG

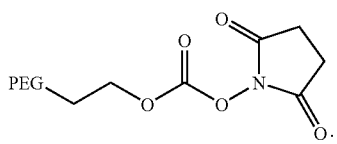

15. The process of claim 1, wherein said multi-functional linking moiety having at least one functional group being unreactive with said activated polymer residue is selected from the group consisting of substituted alkyl diamines, triamines, natural and unnatural amino acid derivatives and malonic ester derivatives.

16. The process of claim 15, wherein said multi-functional linking moiety having at least one functional group being unreactive with said activated polymer residue is selected from lysine, diamino alkyls, dihydroxyalkyls, and dithioakyls.

17. The process of claim 15, wherein the multi-functional aliphatic linking moiety having at least one functional group being unreactive with said activated polymer residue is lysine, a lysine ester or a lysine ethyl ester.

18. The process of claim 1, wherein said first quenching agent is a compound containing a free amine, free thiol or free hydroxyl group.

19. The process of claim 18, wherein said first quenching agent is selected from the group consisting of cysteine, benzyl amine, n-butyl amine, phenylethylamine, C-terminal protected amino acids and mixtures thereof.

20. The process of claim 1, wherein said second quenching agent is a compound containing a silyl group or an acid chloride.

21. The process of claim 20, wherein said second quenching agent is selected from the group consisting of TBDM-SiCl, TMSiCl, MeI, MeSO$_4$, CF$_3$SO$_3$Me, and Me$_3$OBF$_4$.

22. The process of claim 21, wherein said second quenching agent is TBDMSiCl.

23. The process of claim 1, wherein the compound capable of activating the deprotected intermediate polymer conjugate is N-hydroxysuccinimide (NHS).

24. The process of claim 2, wherein the biologically active compound is selected from proteins, peptides polypeptides, enzymes, oligonucleotides, single chain binding antigens (SCA's), antibodies, antibody fragments and natural or synthetic medicinal chemicals.

25. The process of claim 24, wherein the protein is an interferon.

26. The process of claim 25, wherein the interferon is α, β or γ interferon.

27. The process of claim 2, wherein the polymer conjugates are selected from the group consisting of

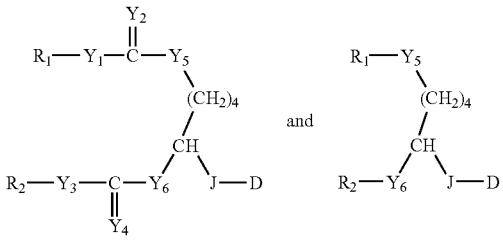

wherein

R$_{1-2}$ are the same or different polymeric residues;

Y$_{1-6}$ are independently O, S, or NR$_{10}$, wherein R$_{10}$ is selected from the group consisting of H, C$_{1-6}$ alkyls and substituted alkyls, C$_{3-6}$ branched alkyls and substituted branched alkyls and C$_{4-8}$ cycloalkyls;

J is a bifunctional linking moiety; and

D is a biologically active compound, targeting moiety or diagnostic agent.

28. The process of claim 1, wherein the activatable polymer residue is mPEG-OH; the activating agent capable of providing a leaving group is N-hydroxysuccinimidyl; the activated polymer residue is mPEG-succinimidyl carbonate, the first quenching agent is benzyl amine; the second quenching agent is TBDMSiCl; and the compound capable of activating the deprotected intermediate polymer for linking to a biological moiety is N-hydroxysuccinimidyl.

29. The process of claim 28 wherein the N-hydroxysuccinimidyl activated intermediate polymer conjugate is further reacted with a biologically active compound.

30. A process for preparing an activated polymer having a multifunctional linking moiety thereon, comprising:

a) reacting an activatable polymer residue with an activating agent capable of providing a leaving group thereon to provide a first reaction mixture containing an activated polymer residue and said activatable polymer residue;

b) reacting said first reaction mixture with a multi-functional linking moiety having a protecting group thereon which is unreactive with said activated polymer residue under conditions wherein said activated polymer residue of the first reaction mixture is present in excess with respect to said multi-functional linking moiety to form a second reaction mixture containing said first reaction mixture and an intermediate polymer containing the protecting group resulting from said reacting of said activated polymer residue with said multi-functional linking moiety;

c) quenching said second reaction mixture with a sufficient amount of a first quenching agent to inactivate the activatable polymer residue therein forming a third reaction mixture containing said intermediate polymer;

d) adding a sufficient amount of a second quenching agent to said third reaction mixture to inactivate the activated polymer residue therein and form a fourth reaction mixture containing said intermediate polymer;

e) removing the protecting group from the intermediate polymer and neutralizing said fourth reaction mixture to form a fifth reaction mixture containing a deprotected intermediate polymer; and f) reacting said fifth reaction mixture with a compound capable of activating the deprotected intermediate polymer therein for linking to a biologically active moiety and form a sixth reaction mixture containing an activated polymer having a multifunctional linking moiety thereon.

* * * * *

UNITED STATES PATENT AND TRADEMARK OFFICE
CERTIFICATE OF CORRECTION

PATENT NO. : 7,365,127 B2  Page 1 of 1
APPLICATION NO. : 11/051009
DATED : April 29, 2008
INVENTOR(S) : Dechun Wu et al.

It is certified that error appears in the above-identified patent and that said Letters Patent is hereby corrected as shown below:

Column 16, line 53 in claim 11,
"mPEG-SO$_2$" should read -- mPEG-SH --.

Column 18, line 20 in claim 24,
"peptides polypeptides" should read -- peptides, polypeptides --.

Signed and Sealed this

Seventh Day of October, 2008

JON W. DUDAS
*Director of the United States Patent and Trademark Office*